United States Patent [19]

Payne et al.

[11] Patent Number: 5,172,193
[45] Date of Patent: Dec. 15, 1992

[54] METHOD OF PREDICTING CUT-TIME OF MILK COAGULUM IN CHEESE-MAKING PROCESS

[75] Inventors: Frederick A. Payne; Clair L. Hicks, both of Lexington, Ky.

[73] Assignee: University of Kentucky Research Foundation, Lexington, Ky.

[21] Appl. No.: 480,629

[22] Filed: Feb. 15, 1990

[51] Int. Cl.$^5$ .............................................. G01N 21/55
[52] U.S. Cl. ..................... 356/445; 356/448; 73/64.1; 73/169; 73/64.43; 250/574
[58] Field of Search ............. 356/445, 446, 447, 448, 356/39, 40, 41; 73/64.1, 169; 250/564, 574

[56] References Cited

U.S. PATENT DOCUMENTS 4,542,645  9/1985  Richardson et al.
4,607,955  8/1986  Corbett.
4,677,298  6/1987  Zelmanovic et al.

FOREIGN PATENT DOCUMENTS 8203460  10/1982  PCT Int'l Appl. ................ 356/436

OTHER PUBLICATIONS

Fundamentals of Dairy Chemistry—3rd edition—Noble P. Wong—editor—Van Nostrand Reinhold Co., Inc., 1988, pp. 620–625.

Primary Examiner—Samuel A. Turner
Assistant Examiner—LaCharles P. Keesee
Attorney, Agent, or Firm—King & Schickli

[57] ABSTRACT

An apparatus for predicting milk coagulum cut-time in a cheese making process includes a light source, a sensor or detector for sensing diffuse reflectance of light from said milk and a controller for analyzing the diffuse reflectance and accurately predicting the cut-time to significantly enhance overall yield. More specifically, the apparatus includes an optical probe which may be suspended over the milk or attached to a wall of a fermentation vessel in which the milk is contained. A method for predicting milk coagulum cut-time includes the steps of (a) directing light from a light source toward milk undergoing enzymatic hydrolysis; (b) sensing diffuse reflectance of that light from the milk; (c) analyzing the sensed diffuse reflectance profile and (d) signaling the cut-time. The sensing occurs at between 400 to 6000 nm. Specific mathematical formulae for the analyzing steps are also disclosed.

11 Claims, 4 Drawing Sheets

Diffuse reflectance, first derivative and second derivative for milk coagulation at 32°C and rennet concentration of 0.50 ml/kg.

A schematic of the diffuse reflectance profile for milk coagulation showing the induction, sigmoidal, and logarithmic periods.

A plot of the test data showing the correlation between observed cut-time and time period to maximum first derivative.

METHOD OF PREDICTING CUT-TIME OF MILK COAGULUM IN CHEESE-MAKING PROCESS

TECHNICAL FIELD

The present invention relates generally to an apparatus and method for improving the productivity of the cheese making process and, more particularly, to an apparatus and method for accurately predicting the optimum milk coagulum cut-time.

BACKGROUND OF THE INVENTION

The first major step in the cheese making process is the coagulation of the milk by enzymatic hydrolysis of K-casein. To achieve this end, enzyme extracts from calf stomachs, microbially produced enzymes or other enzymes are utilized. The hydrolysis of K-casein leads to destabilization of the colloidal system of the milk. This is followed by aggregation of the micelles into clusters. Over time, the clusters grow in size. This growth in size is followed by crosslinking between chains which eventually transforms the milk into a gel or coagulum.

Once a desired point is reached in the coagulation process, the coagulum is "cut" by traversing with wire knives to slice the coagulum into approximately 0.7 cm cubes. The coagulating matrix then shrinks during further processing and as a result forces liquid from the cubes. Consequently, a two phase system of curd and whey results. The textural strength or firmness of the curd increases with time.

Selection of the optimum point to cut the coagulum has been a subject of much research. It has been shown that coagulum strength at cutting effects the recovery of milk components during cheese making. More particularly, milk components not entrapped in the K-casein matrix are lost into the whey. Thus, cutting the coagulum when extremely soft decreases cheese yield due to the increased loss of fat and curd fines. Conversely, cutting when the coagulum is too firm retards syneresis and results in high moisture cheese. Further, it has also been suggested that coagulum strength affects the quality of the resulting cheese.

Curd firmness and the rate of firming are affected by many factors. For example, high K-casein concentration increases curd firmness. The time and temperature of milk storage prior to cheese manufacture also affects curd firmness. Homogenization and standardization may also influence coagulum firmness. Other factors affecting firmness are the breed of cow from which milk is collected, period of lactation of the cow, milk quality and type of enzyme used in cheese making.

Cheese makers conventionally cut the coagulum 25 to 30 minutes after adding the enzyme to conform to factory schedules. As indicated above, however, the factors that influence firmness vary depending on milk source and treatments. Thus, coagulum cut 30 minutes after enzyme addition may not always be of a consistent strength. As a result, a need is identified for a sensor which will monitor milk coagulation and compensate for fluctuations in pH, temperature, enzyme activity, differences in milk and other relevant factors to allow the coagulum to be cut at a consistent condition near the optimum point for cheese production. In this way losses may be prevented due to inadequate enzyme addition and other factors may be addressed to increase overall yields.

To meet this need, a number of devices have been employed to measure coagulum strength with the object of predicting the cut-time. One such device is disclosed in U.S. Pat. No. 4,542,645 to Richardson et al. The apparatus disclosed in the Richardson et al. patent includes a substantially flat dish-shaped probe member that is suspended from a wire by a connecting rod into a enzymatic hydrolysis vessel filled with milk. The probe is reciprocated through a small vertical distance within the coagulating milk in the vessel. The increasing resistance to the probe manipulation is communicated through the wire as the milk coagulates. The resistance is measured and when it reaches a predetermined value, it is time to cut the coagulum.

While providing some guidance in establishing when to cut the coagulum, the Richardson et al. device unfortunately physically disrupts the coagulum and is sensitive to environmental vibrations. As such, it does not always provide a fully accurate measurement of coagulation and is considered a destructive test. Preferably, a continuous monitor should be non-destructive and accordingly, a need is identified for just such a monitor.

SUMMARY OF THE INVENTION

Accordingly, it is a primary object of the present invention to provide an apparatus and method for predicting cut-time of milk coagulum in a cheese making process overcoming the above-described limitations and disadvantages of the prior art.

An additional object of the present invention is to provide a simple and inexpensive apparatus and method for accurately predicting the cut-time of milk coagulum in the cheese making process.

Another object of the present invention is to provide an apparatus for accurately predicting coagulum cut-time to achieve maximum yield in the cheese making process.

Yet another object of the present invention is to provide an apparatus and method for the non-destructive or non-invasing monitoring of milk coagulum so as to allow an accurate prediction of cut-time without adversely effecting the coagulation process.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an apparatus is provided for predicting milk coagulum cut-time in a cheese making process. The apparatus includes a light source and means for directing light from the source to milk undergoing enzymatic hydrolysis. The apparatus also includes means for collecting diffusely reflected light from the milk and directing it to a sensor. Further, a controller is provided for analyzing the diffuse reflectance to accurately predict cut-time and thereby significantly enhance overall production yields.

More particularly, the apparatus includes an optical probe. The optical probe may either be suspended over the milk undergoing enzymatic hydrolysis or, more preferably, mounted to a wall of the fermentation vessel holding the milk. The probe is connected to the light source and the sensing means by means of a fiber optic link. Preferably, the diffuse reflectance of the light is monitored or sensed. at substantially between 400 and 6000 nm wavelength. Still more preferably, the reflectance is monitored at substantially 950±5 nm wavelength.

In accordance with yet another aspect of the present invention, the apparatus includes a signaling means such as an alarm or other electronically activated device. The sounding of the alarm signals the time for cutting the coagulum in order to obtain the highest yields of consistently high quality cheese.

In accordance with yet another aspect of the present invention, a method for predicting milk coagulum cut-time in a cheese making process is provided. The method includes the steps of directing light from a light source toward milk undergoing enzymatic hydrolysis and simultaneously sensing the level of diffusely reflected light from the milk. Next is the step of analyzing the sensed diffuse reflectance profile of the light. Additionally, this method includes the signaling of the cut-time such as by the sounding of an alarm as discussed above.

More particularly, the analyzing step may be completed in accordance with a number of mathematical formulas. For example, analysis may be completed in accordance with the formula:

$$(dV/dt)_{max} \times t_c = C$$

where:
$t_c$ = predicted cut-time in minutes
$(dV/dt)_{max}$ = maximum value of the first derivative where V = output voltage of the sensor in volts and t = time in minutes
C = constant = 12.11

Alternatively, the formula utilized may be as follows:

$$(t_c - t_i)\left[\left(\frac{dV}{dt}\right)_{max}^a\right] = C$$

where:
t = predicted cut-time in minutes
$t_1$ = induction time in minutes $\left(\frac{dV}{dt}\right)_{max}$ = maximum value of the first derivative where V = output voltage of the sensor in volts and t = time in minutes a = exponent = 1.95
C = constant = 3.93

Still another alternative formula is:

$$\frac{R_\infty - R}{R_\infty - R_o} = e^{-((t-t_o)/\tau)}$$

where:
R = reflectance ratio from the sensor
$R_\infty$ = theoretical reflectance ratio after an infinitely long period of coagulation
$\tau$ = gelling time constant in minutes and a multiple of the cut-time, $t_c$
t = time since enzyme addition in minutes $t_o$ = time since enzyme addition to end of transition period in minutes
$R_o$ = reflectance ratio at end of transition period Yet another alternative formula is:

$$t_c 2.67 t_{max} - 4.2$$

where:
$t_{max}$ = time from enzyme addition to maximum first derivative in minutes
t = predicted cut-time in minutes Still other objects of the present invention will become readily apparent to those skilled in the art from the following description wherein there is shown and described a preferred embodiment of this invention, simply by way of illustration of one of the modes best suited to carry out the invention. As it will be realized, the invention is capable of other different embodiments and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a part of the specification, illustrates several aspects of the present invention, and together with the description serves to explain the principles of the invention. In the drawing.

Reference will now be made in detail to the present preferred embodiment of the invention, an example of which is illustrated in the accompanying drawing.

DETAILED DESCRIPTION OF THE INVENTION

Figure 1:
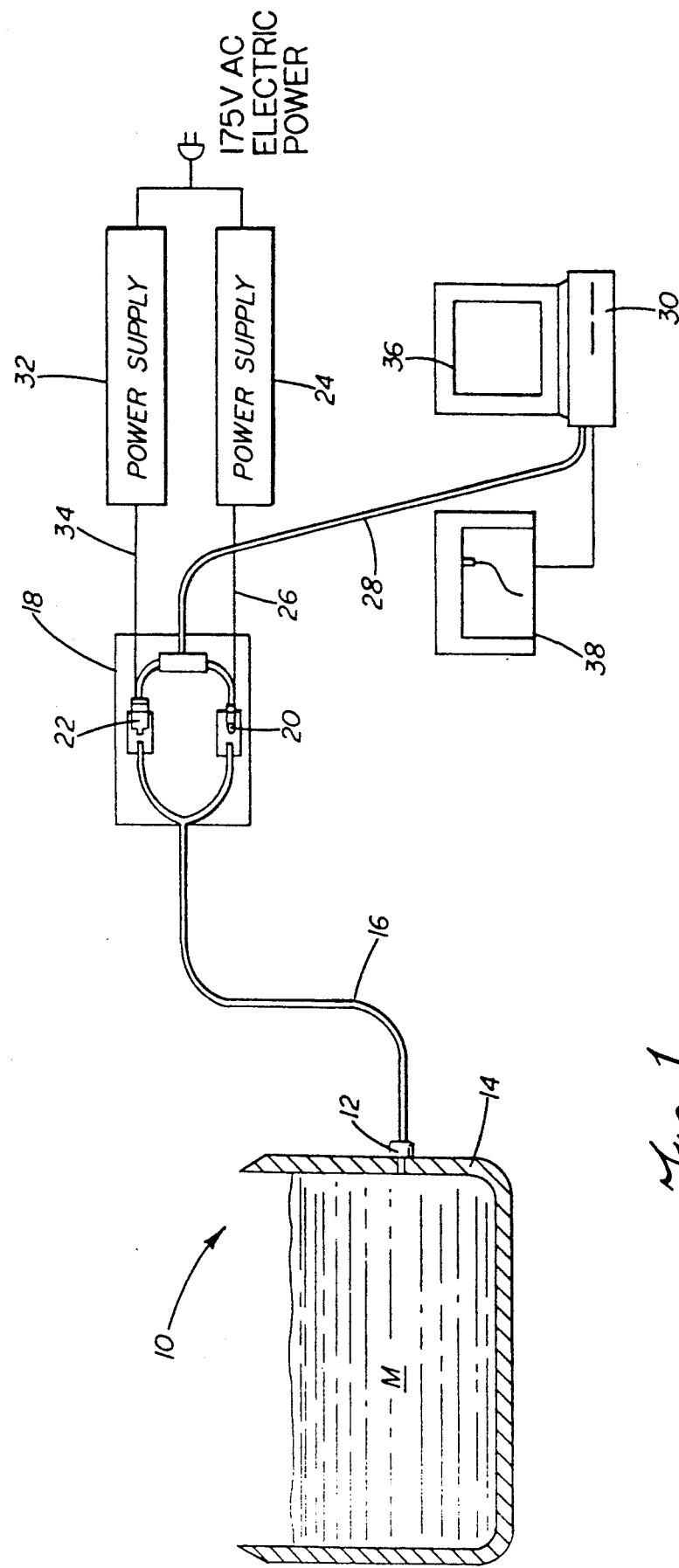
FIG. 1 is a combined partially sectional, side elevational and schematic view showing the apparatus and control circuit of the present invention.

Reference is now made to the drawing FIG. 1 schematically showing the apparatus 10 of the present invention for accurately predicting the optimum milk coagulum cut-time and thereby improving the overall productivity of the cheese making process. The apparatus 10 includes an optical probe 12 which is shown mounted to a wall of a enzymatic hydrolysis vessel 14 holding milk M undergoing processing. Preferably, the optical probe 12 is mounted with a clean-in-place mounting meeting USDA, Triple A sanitation requirements. As an alternative, however, the optical probe 12 could simply be suspended over the vessel 14 near the upper surface of the milk M. With either mounting, the milk coagulum may be monitored in situ in the enzymatic hydrolysis vessel 14 non-invasively/non-destructively.

The optical probe 12 is connected by means of a fiber optic link 16 to an emitter/detector box 18. The emitter/detector box 18 includes a light source 20 and light sensor 22. The fiber optic link 16 comprises two separate bundles of fibers which may contain one or multiple fibers in each bundle. One fiber bundle carries light from the source 20 to the optical probe 12 which directs the light into the milk M in the vessel 14. The other fiber bundle carries the light reflected by the milk M back to the sensor 22. The fiber optic bundles in the link 16 are protected from damage by their sheathing, as well as an outer metal conduit.

The emitter/detector box 18 is designed to shield the enclosed electronics from electrical noise. Further, the emitter/detector box 18 may be remotely located from the enzymatic hydrolysis vessel 14 so as to protect the sensitive components from potential moisture damage.

More preferably, the light source 20 may assume the form of a sub-miniature, incandescent, read-out lamp rated at 2.5 volts and 0.40 amps such as is available from the Wagner Division of Cooper Industries of Parsippany, N.J. Such a read-out lamp has a plastic encapsulated base with connecting leads and is mounted in a fiber optic terminator within the emitter/ detector box 18. A set screw is used to secure the light source firmly to the fiber optic terminator. A lamp of the type described has a rated light output of approximately 1,250 ft-cd, most of which is in the infrared region of the spectrum. Other sources such as infrared light emitting diodes (LED) may be employed as a light source.

The light source 20 is supplied with a constant current by a power supply 24 of the type known in the art through power line 26. More particularly, the power supply 24 may take the form of a precision current regulator circuit built around a three-terminal adjustable positive voltage regulator, the LM 317, (Voltage Regulator Handbook, National Semiconductor Corporation, Santa Clara, CA, 1982). The function of this circuit is to supply the light source 20 with the appropriate amount of current which varies minimally in time. The current components at the operating point of the LM 317 are chosen with this objective. The LM 317 develops a nominal constant reference voltage at 1.25 volts between its $V_{out}$ and $V_{adj}$ terminals. This reference voltage is impressed across a program resistor causing a current to flow through it.

Preferably, the resistor is a precision wire wound resistor having a value of 4 ohms±1%, 1W. Its temperature coefficient of resistance is 5 ppm/° C. A fan (not shown) may be mounted to the power supply 24 to ensure adequate air flow around the power supply to minimize variation of temperature of the resistor due to self heating. As described, the current I is equal to 1.25V/4 ohms is substantially constant at 312.5 mA± 1%. The adjustment pin current of the LM 317 has a typical value of 50 μA. The LM 317 is used under operating conditions for which the data sheets specify typical variation in the adjustment pin current of 0.2μ A, the maximum variation specified being 5 μA. Thus, the variation in the value of the light source current is minimal.

Preferably, the detector 22 is a solid state integrated optical detector such as manufactured by E.G. & G. Photon Devices of Salem, MA (Part No. DFA 9500-8825). The active element in the DFA 9500 is a photodiode operated in the photoconductive mode, that is, an external bias is applied to it in the reverse direction at its p-n junction. The current flowing from the photodiode when it is illuminated is composed of a photoinduced current and a reverse leakage current. While the former varies linearly with the incident light, the latter remains constant for fixed bias and fixed temperature conditions.

In addition to the photodiode, the DFA 9500 has a low noise FET input amplifier and an optical filter built into it. The photodiode is used in conjunction with the amplifier to form a current-to-voltage converter. The output voltage of the amplifier is proportional to the current from the photodiode and the proportionality factor is decided by an external feedback resistor. The interference filter has a center wavelength of 950 nm with a band width of 10 nm. Thus, at the output pins of the DFA 9500, an analog voltage proportional to the incident light in the pass band of the filter is available. This output voltage is transmitted through a cable 28 to a controller 30. A 741 op-amp (Linear Data Book—National Semiconductor Corporation, Santa Clara, CA, 1982) configurative as a voltage follower is used between the sensor 22 and the cable 28 and acts as a buffer. Another useful feature built into the DFA 9500 is an offset voltage control. The 25 K ohm potentiometer can be used to adjust the output voltage of the DFA 9500 to 0 volts when there is no incident light.

The DFA 9500 comes in a ten pin, TO-10 case and is mounted on a ten pin plastic base. It is secured firmly in its fiber optic terminator by means of a set screw. Electrical connections are made to it by soldering connecting wires to the pins of the base. A separate power supply 32 supplies the DFA 9500 with a stable +15 V and −15 V through the power line 34.

The signal from the detector is transmitted along the cable 28 to the controller 30 for analysis. Preferably, the controller 30 is in the form of a microprocessor such as an IBM PS/2 Model 30. More specifically, a multi-function analog-digital expansion board for IBM PC compatible computers called DASCON-1 (Metrabyte Corporation, Taunton, Mass.) may be used to read voltages from the sensor 22. In practice, the DASCON-1 is plugged into one of the expansion slots within the computer and requires 15 consecutive address locations in the I/0 address space of the computer. External inputs to the DASCON-1 may be applied through a 37 pin D connector. The DASCON-1 includes a four channel, 12 bit plus sign, dual slope A/D converter. The A/D converter has a resolution of 500 microvolts and the full scale input of each channel is ±2.0475 volts.

As shown in FIG. 1, data acquired by the sensor 22 and interpreted by the controller 30 may be graphically presented on a CRT 36 and/or recorded by a strip chart recorder 38.

Figure 2:
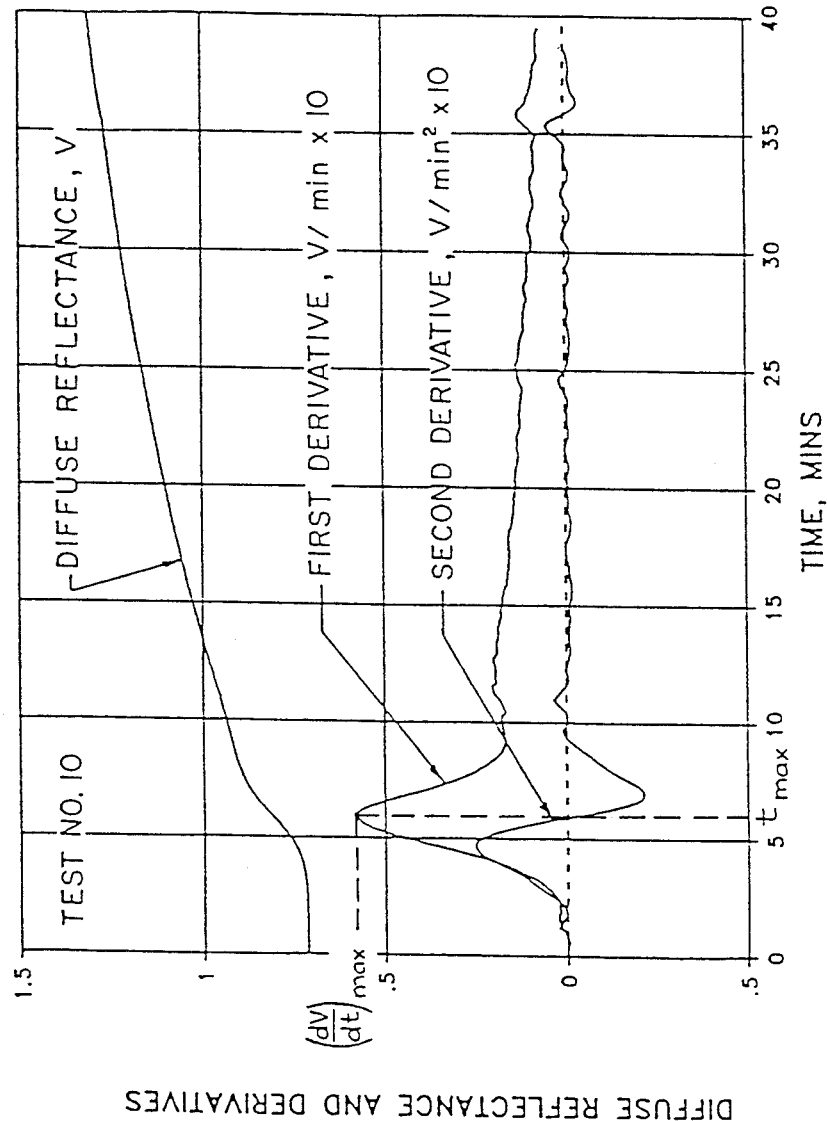
FIG. 2 is a graphic representation of the sensor output for diffuse reflectance as measured in volts and the first and second derivatives.
Figure 3:
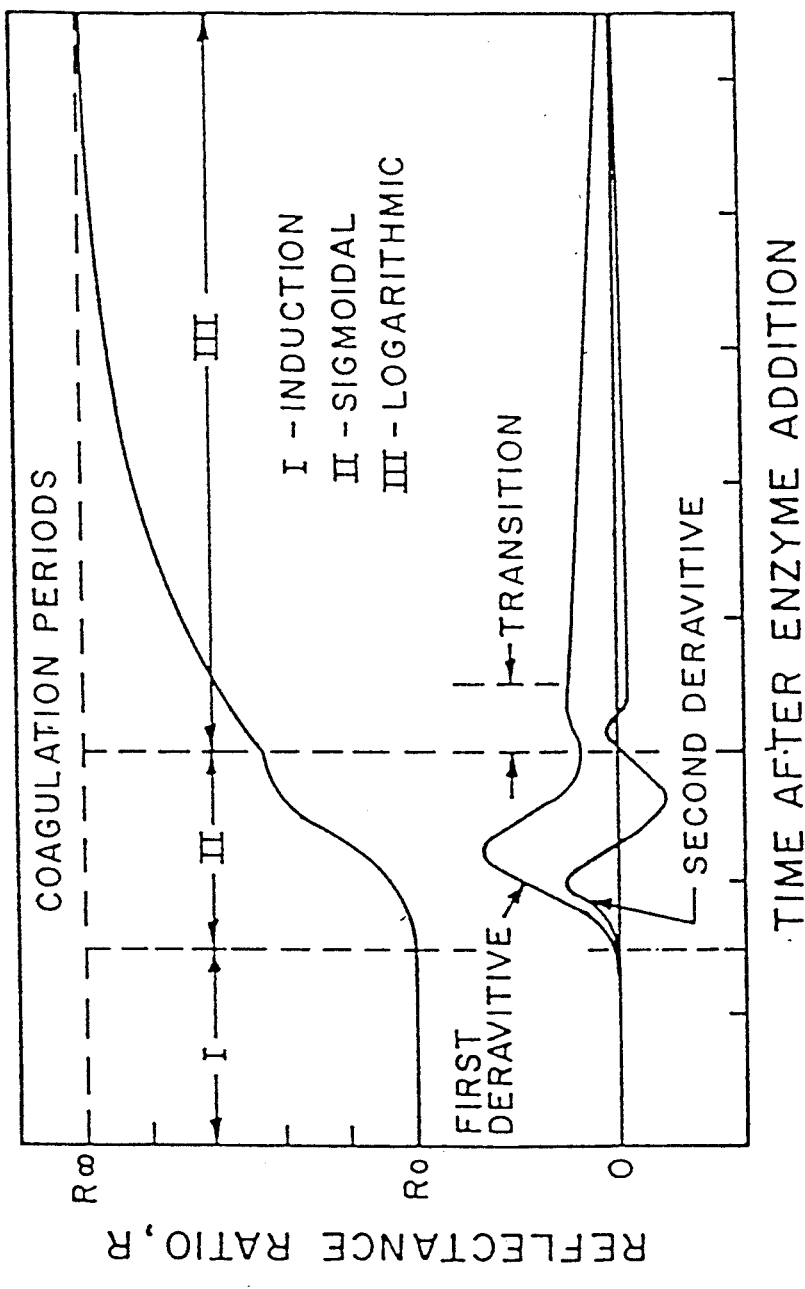
FIG. 3 is a graphic representation of the diffuse reflectance profile clearly identifying the induction, sigmoidal and logarithmic periods.

Utilization of the apparatus 10 to monitor the diffuse reflectance of milk undergoing enzymatic hydrolysis is best described by referencing. FIGS. 2 and 3. FIG. 2 shows the output of the sensor 22 for diffuse reflectance as measured in volts and the first and second derivatives. The reflectance profile is simplified by plotting the reflectance ratio (R) which is the ratio of the observed sensor output divided by the initial sensor output. R is thus a measure of the increase in reflectance. Analysis of the reflectance profile shows that it may be divided into three periods which are shown in FIG. 3 and labeled the induction, sigmoidal and logarithmic periods. The induction period is considered the time during which the enzyme is hydrolyzing the casein micelles and there is no change in diffuse reflectance. It is thought the sigmoidal period begins when the hydrolyzed casein micelles begin to form microflocs which change the diffuse reflectivity of the milk. As the microflocs continue to grow, gelling or crosslinking begins. This initiates the logarithmic period. As the crosslinking sites are depleted, the diffuse reflectance approaches an asymptotic value.

vessel wall for a distance of about 3/16" without tearing. The test results are provided in Table 1 below.

TABLE 1

| Test No. | Milk Temp. °C. | Enzyme Concen., ml/kg | $\left(\frac{dV}{dt}\right)_{max}$ V/min × 10 | Observed Cut-Time $t_c$, min | Predicted Cut Time per Formula 1 $t_c$, min |
| --- | --- | --- | --- | --- | --- |
| 1 | 32 | 0.25 | 0.37 | 30.0 | 33.02 |
| 2 | 32 | 0.25 | 0.37 | 29.5 | 33.02 |
| 3 | 37 | 0.25 | 0.66 | 20.1 | 18.51 |
| 4 | 37 | 0.25 | 0.68 | 20.5 | 17.97 |
| 5 | 27 | 0.25 | 0.16 | 76.0 | 76.38 |
| 6 | 27 | 0.25 | 0.16 | 82.5 | 76.38 |
| 7 | 32 | 0.50 | 0.55 | 20.0 | 22.22 |
| 8 | 32 | 0.50 | 0.57 | 21.2 | 21.44 |
| 9 | 32 | 0.125 | 0.25 | 51.0 | 48.88 |
| 10 | 32 | 0.125 | 0.25 | 48.4 | 48.88 |

It has now been found that the characteristics of the reflectance profile during the sigmoidal period may be used to accurately predict the curd or coagulum cut-time. More specifically, but not exclusively, it has been found that the peak value of the first derivative may be used to predict cut-time.

Accordingly, the method of the present invention may include the step of analyzing the sensed diffuse reflectance profile of the light in accordance with the following mathematical formulation:

$$\left(\frac{dV}{dt}\right)_{max} \times t_c = C \qquad (1)$$

where
$t_c$ = predicted cut-time in minutes
$(dV/dt)_{max}$ = maximum value of the first derivative where $V$ = output voltage of the sensor in volts and $t$ = time in minutes.
$C$ = constant = 12.11

This may be accomplished by programming the controller 30 with appropriate software for this purpose. Results of ten tests designed to evaluate the response of the milk coagulation sensor apparatus 10 over a range of temperatures and enzyme concentrations and analyzed in accordance with formula 1 are set forth in Example 1 below.

EXAMPLE 1

Milk was collected, skimmed and pasteurized at low temperature (63° C. for 30 minutes). The milk was then stored at 4° C. until used. The temperatures selected for testing were 27°, 32° and 37° C. The enzyme used was single strength rennet extract (Marshall Laboratories, Lot No. 004028). The enzyme concentrations tested were 0.125, 0.25 and 0.50 ml/kg of milk. The tests were conducted over a 32-hour period to minimize the effect of biological changes in the milk. The milk had a fat content of 0.5% and a pH of 6.8.

The single strength rennet was diluted with water for each test such that 1 ml of the dilution was added to 800 ml of milk. The milk was heated to the test temperature ±0.1° C., placed in a water bath, and covered with an insulating board to prevent surface cooling. The enzyme was added and the milk stirred for 30 seconds. The time clock and data acquisition were initiated immediately upon addition of the enzyme. The "cut-time" was subjectively determined during each test. The cut-time was determined as the time when the curd could be pulled with a spatula from the enzymatic hydrolysis In accordance with an alternative method of the present invention, the step of analyzing the sensed diffuse reflectance profile of the light is completed in accordance with the following mathematical formulation:

$$(t_c - t_i)\left[\left(\frac{dV}{dt}\right)_{max}\right]^a = c \qquad (2)$$

where
$t_c$ = predicted cut-time in minutes
$t_i$ = indication time in minutes = 15.0

$\left(\frac{dV}{dt}\right)_{max}$ = maximum value of the first derivative where $V$ = output voltage of the sensor in volts and $t$ = time in minutes $a$ = exponent = 1.95
$c$ = constant = 3.93

Results of the tests described in Example 1 and analyzed in accordance with formula 2 are set forth in Table 2 below.

TABLE 2

| Test No. | Milk Temp. °C. | Enzyme Concen. ml/kg | Observed Cut-Time $t_c$, min. | Predicted Cut Time per Formula 2, min. |
| --- | --- | --- | --- | --- |
| 1 | 32 | 0.25 | 30.0 | 29.6 |
| 2 | 32 | 0.25 | 29.5 | 30.0 |
| 3 | 37 | 0.25 | 20.1 | 20.0 |
| 4 | 37 | 0.25 | 20.5 | 19.6 |
| 5 | 27 | 0.25 | 76.0 | 81.2 |
| 6 | 27 | 0.25 | 82.5 | 80.7 |
| 7 | 32 | 0.50 | 20.0 | 21.6 |
| 8 | 32 | 0.50 | 21.2 | 21.0 |
| 9 | 32 | 0.125 | 51.0 | 48.0 |
| 10 | 32 | 0.125 | 48.4 | 46.4 |

There are innumerable mathematical models that could be used to relate the peak of the first derivative to the cut-time. The above formulas 1 and 2 are just two examples. Additionally, it should be appreciated that other curve characteristics could be correlated to arrive at the cut-time. Examples include the area under the reflectance profile curve to a specified point, the area under the second derivative curve and the momentum of the curve areas. A unique aspect of this invention is that the curve characteristics of the sigmoidal period can be used to accurately predict coagulum cut-time.

Further investigation yielded the finding that the logarithmic period may also be related to cut-time. The following non-linear formula may be programmed into the controller 30 on software to analyze the reflectance profile and predict the cut-time.

$$\frac{R_\infty - R}{R_\infty - R_o} = e^{-((t-t_0)/\tau)} \quad (3)$$

where

Figure 4:
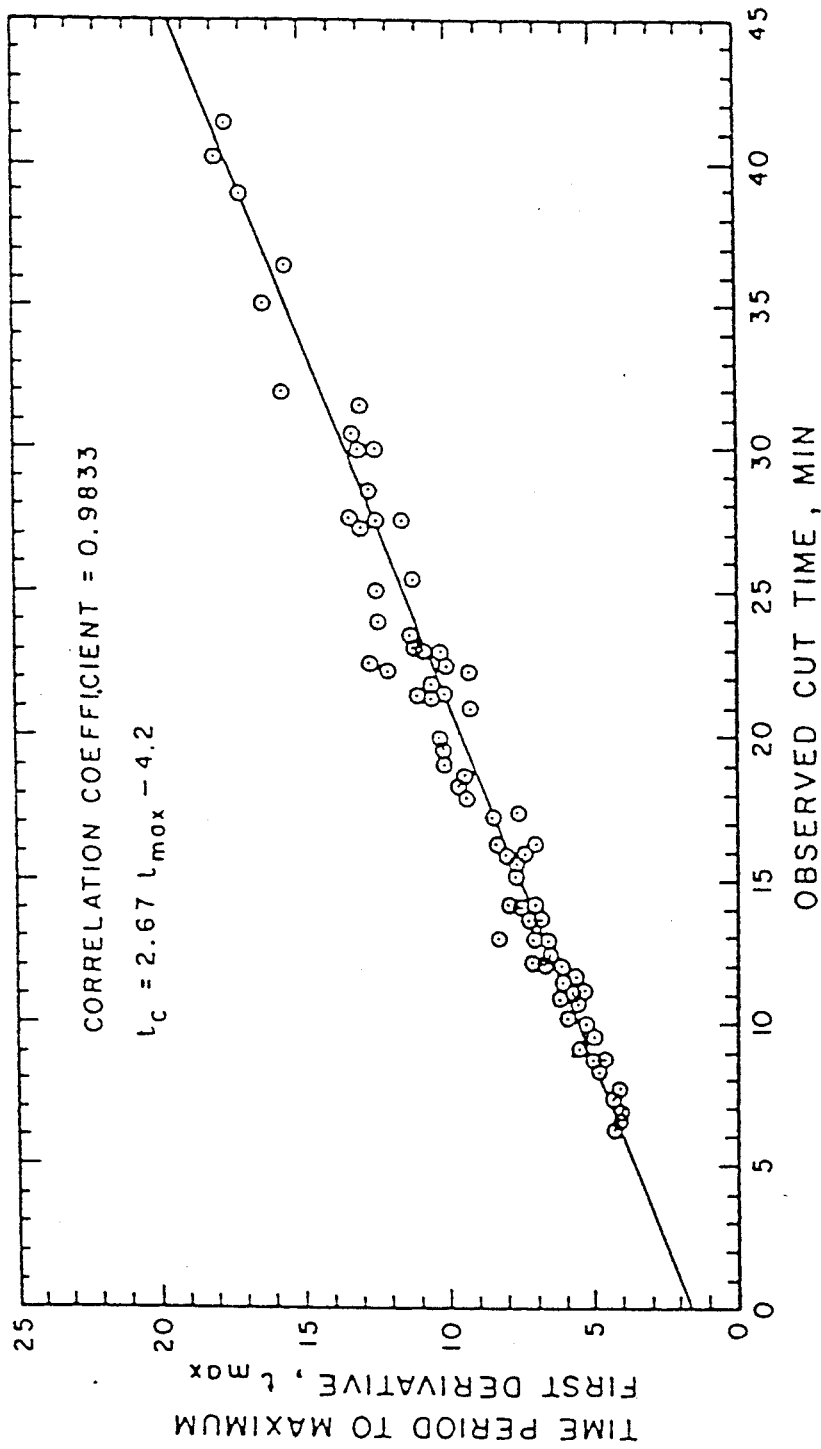
FIG. 4 is a graphic representation showing the correlation between observed cut-time and time period to maximum first derivative.

R = reflectance ratio from sensor
$R_\infty$ = theoretical reflectance ratio after an infinitely long period of coagulation
$\tau$ = gelling time constant in minutes which is a multiple of the cut-time, $t_c$
t = time since enzyme addition in minutes
$t_o$ = time since enzyme addition to end of transition period in minutes
$R_o$ = reflectance ratio at end of transition period A strong correlation between two other time periods was also observed. The first period is the time from enzyme addition to the time when the first derivative of the reflectance profile reaches a maximum (see FIG. 2). The maximum value of the first derivative also occurs when the second derivative crosses zero. The second is the time from enzyme addition to the cut-time observed by the trained specialist. FIG. 4 shows the correlation between these times. Statistical analysis showed that these times have a correlation coefficient of 0.9833.

This correlation can be used to predict cut-time by programming the controller 30 with software based upon the following formula:

$$t = 2.67\, t_{max} - 4.2$$

where:

$t_{max}$ = time from enzyme addition to maximum first derivative in minutes
$t_c$ = predicted cut-time in minutes In summary, numerous benefits result from employing the concepts of the present invention. More specifically, the present invention provides both an apparatus and method for continuously and non-destructively monitoring milk undergoing enzymatic hydrolysis. The invention advantageously allows the accurate prediction of the optimum coagulum cut-time to improve the overall quality of the cheese product while also maximizing productivity and reducing waste. The invention also substantially eliminates the need to have a trained specialist monitor the milk throughout enzymatic hydrolysis thereby significantly lowering labor costs.

The foregoing description of a preferred embodiment of the invention has been presented for purposes of illustration and description. It is not intended to be exhaustive or to limit the invention to the precise form disclosed. Other modifications or variations are possible in light of the above teachings. The embodiment was chosen and described to provide the best illustration of the principles of the invention and its practical application to thereby enable one of ordinary skill in the art to utilize the invention in various modifications as are suited to the particular use contemplated. All such modifications and variations are within the scope of the invention as determined by the appended claims when interpreted in accordance with the breadth to which they are fairly, legally and equitably entitled.

We claim:

1. A method for predicting mild coagulum cut-time in a cheese making process, comprising the steps of:
   directing light from a light source toward milk undergoing enzymatic hydrolysis;
   sensing diffuse reflectances of the light from said milk at substantially 950±5 nm;
   analyzing the sensed diffuse reflectance profile of said light; and
   signaling said cut-time.

2. The method as set forth in claim 1, wherein said analyzing step is completed in accordance with the following formula:

$$\left(\frac{dV}{dt}\right)_{max} \times t_c = C$$

where:

$t_c$ = predicted cut-time in minutes
$(dv/dt)_{max}$ = maximum value of first derivative where V = output voltage of the sensor in volts and t = time in minutes
C = constant = 12.11

3. The method set forth in claim 1, wherein said analyzing step is completed in accordance with the following formula:

$$(t_c - t_i)\left[\left(\frac{dV}{dt}\right)_{max}^{a}\right] = C$$

where:

$t_c$ = predicted cut-time in minutes
$t_i$ = induction time in minutes $\left(\frac{dV}{dt}\right)_{max}$ = maximum value of the first derivative where V = output voltage of the sensor in volts and t = time in minutes a = exponent = 1.95
C = constant = 3.93

4. The method set forth in claim 1, wherein said analyzing step is completed in accordance with the following formula:

$$\frac{R_\infty - R}{R_\infty - R_o} = e^{-((t-t_0)/\tau)}$$

where:

R = reflectance ratio from the sensor
$R_\infty$ = theoretical reflectance ratio after an infinitely long period of coagulation
$\tau$ = gelling time constant in minutes which is a multiple of the cut-time, $t_c$
t = time since enzyme addition in minutes
$t_o$ = time since enzyme addition to end of transition period in minutes
$R_o$ = reflectance ratio at end of transition period.

5. The method set forth in claim 1, wherein said analyzing step is completed in accordance with the following formula:

$$t = 2.67 t_{max} - 4.2$$

where:

$t_{max}$ = time from enzyme addition to maximum first derivative in minutes $t_c$ = predicted cut-time in minutes

6. A method for predicting milk coagulum cut-time in a cheese making process, comprising the steps of:
- directing light from a light source toward milk undergoing enzymatic hydrolysis;
- sensing diffuse reflectance of said light from said milk;
- analyzing the sensed diffuse reflectance profile of said light;
- identifying induction, sigmoidal and logarithmic periods from the reflectance profile; and
- signaling said cut time.

7. The method as set forth in claim 6, including utilizing characteristics of the sigmodial period of the reflectance profile to accurately predict coagulum cut-time.

8. A method for predicting mild coagulum cut-time in a cheese making process, comprising the steps of:
- directing light from a light source toward milk undergoing enzymatic hydrolysis;
- sensing diffuse reflectance of the light from said milk;
- analyzing the sensed diffuse reflectance profile of said light; and
- signaling said cut-time;
- wherein said analyzing step is completed in accordance with the following formula:

$$(dV/dt)_{max} \times t_c = C$$

where:
- $t_c$ = predicted cut-time in minutes
- $(dV/dt)_{max}$ = maximum value of first derivative where V = output voltage of the sensor in volts and t = time in minutes
- C = constant = 12.11

9. A method for predicting mild coagulum cut-time in a cheese making process, comprising the steps of:
- directing light from a light source toward milk undergoing enzymatic hydrolysis;
- sensing diffuse reflectance of the light from said milk;
- analyzing the sensed diffuse reflectance profile of said light; and
- signaling said cut-time;
- wherein said analyzing step is completed in accordance with the following formula:

$$(t_c - t_i)(dV/dt)_{max}^a = C$$

where:
- $t_c$ = predicted cut-time in minutes
- $(dV/dt)_{max}$ = maximum value of the first derivative where V = output voltage of the sensor in volts and t = time in minutes
- a = exponent = 1.95
- c = constant = 3.93

10. A method for predicting mild coagulum cut-time in a cheese making process, comprising the steps of:
- directing light from a light source toward milk undergoing enzymatic hydrolysis;
- sensing diffuse reflectance of the light from said milk;
- analyzing the sensed diffuse reflectance profile of said light; and
- signaling said cut-time;
- wherein said analyzing step is completed in accordance with the following formula:

$$\frac{R_\infty - R}{R_\infty - R_o} = e^{-((t-t_o)/\tau)}$$

where:
- R = reflectance ratio from the sensor
- $R_\infty$ = theoretical reflectance ratio after an infinitely long period of coagulation
- $\tau$ = gelling time constant in minutes which is a multiple of the cut-time, $t_3$
- t = time since enzyme addition in minutes
- $t_o$ = time since enzyme addition to end of transition period in minutes
- $R_o$ = reflectance ratio at end of transition period

11. A method for predicting mild coagulum cut-time in a cheese making process, comprising the steps of:
- directing light from a light source toward milk undergoing enzymatic hydrolysis;
- sensing diffuse reflectance of the light from said milk;
- analyzing the sensed diffuse reflectance profile of said light; and
- signaling said cut-time;
- wherein said analyzing step is completed in accordance with the following formula:

$$t_c = 2.67 t_{max} - 4.2$$

where:
- $t_{max}$ = time from enzyme addition to maximum first derivative in minutes
- $t_c$ = predicted cut-time in minutes.

* * * * *

UNITED STATES PATENT AND TRADEMARK OFFICE
CERTIFICATE OF CORRECTION

PATENT NO. : 5,172,193
DATED : December 15, 1992
INVENTOR(S) : Frederick A. Payne, Clair L. Hicks It is certified that error appears in the above-indentified patent and that said Letters Patent is hereby corrected as shown below:

Columns 10, 11, and 12: Claims 1,8,9,10 and 11, Line 1, Change "mild" to --milk--.

Column 10, Claim 1, line 5, change "reflectances" to --reflectance--.

Column 12, bewteen lines 1 and 2, should be provided the additional line: --$t_i$ = induction time in minutes--.

Signed and Sealed this

Fourteenth Day of December, 1993

BRUCE LEHMAN

Attest:

Attesting Officer        Commissioner of Patents and Trademarks